United States Patent
Lassoued et al.

(10) Patent No.: US 11,432,762 B2
(45) Date of Patent: Sep. 6, 2022

(54) INTELLIGENT MONITORING OF A HEALTH STATE OF A USER ENGAGED IN OPERATION OF A COMPUTING DEVICE

(71) Applicant: INTERNATIONAL BUSINESS MACHINES CORPORATION, Armonk, NY (US)

(72) Inventors: Yassine Lassoued, Dublin (IE); Julien Monteil, Dublin (IE); Sergiy Zhuk, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 779 days.

(21) Appl. No.: 16/417,460

(22) Filed: May 20, 2019

(65) Prior Publication Data
US 2020/0367807 A1 Nov. 26, 2020

(51) Int. Cl.
*G16H 10/40* (2018.01)
*G16H 20/30* (2018.01)
*G16H 10/60* (2018.01)
*G16H 20/70* (2018.01)
*G16H 50/30* (2018.01)
*A61B 5/00* (2006.01)

(52) U.S. Cl.
CPC .......... *A61B 5/486* (2013.01); *A61B 5/6897* (2013.01); *A61B 5/7267* (2013.01); *A61B 5/7275* (2013.01); *G16H 10/40* (2018.01); *G16H 10/60* (2018.01); *G16H 20/30* (2018.01); *G16H 20/70* (2018.01); *G16H 50/30* (2018.01); *A61B 2503/24* (2013.01)

(58) Field of Classification Search
CPC ................................. G06Q 50/20–26
See application file for complete search history.

(56) References Cited

U.S. PATENT DOCUMENTS

| 2015/0126826 | A1  | 5/2015 | Kaleal et al. |
| 2017/0178052 | A1  | 6/2017 | Durham et al. |
| 2018/0107984 | A1  | 4/2018 | Bender et al. |
| 2019/0080055 | A1* | 3/2019 | Bettencourt Da Silva ................. G16H 40/63 |
| 2019/0108913 | A1* | 4/2019 | Coke .................... A61B 5/0205 |
| 2019/0209022 | A1* | 7/2019 | Sobol .................. A61B 5/7267 |

OTHER PUBLICATIONS

"System and method for mapping biometric stress levels to computer activity", Authors et. al.: Disclosed Anonymously. IP.com Electronic Publication Date: Jun. 12, 2014 ( 4 Pages ).

* cited by examiner

*Primary Examiner* — Neal Sereboff
(74) *Attorney, Agent, or Firm* — Griffiths & Seaton PLLC

(57) ABSTRACT

Embodiments for intelligent monitoring of a health state of a user by a processor. A health state of a user may be learned while engaged in one or more activities associated with a computing device. One or more mitigating actions may be identified and recommended to implement by the user to minimize one or more possible negative impacts upon the health state of the user while engaged in the one or more activities associated with the computing device.

7 Claims, 7 Drawing Sheets

INTELLIGENT MONITORING OF A HEALTH STATE OF A USER ENGAGED IN OPERATION OF A COMPUTING DEVICE

BACKGROUND OF THE INVENTION

Field of the Invention

The present invention relates in general to computing systems, and more particularly to, various embodiments for intelligent monitoring of a health state of a user while engaged in use of a computing device.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field. As great strides and advances in technologies come to fruition, the greater the need to make progress in these systems advantageous for efficiency and safety such as, for example, for using the vast amount of available data to recognize and mitigate adverse impacts on a well-being or health of a person.

SUMMARY OF THE INVENTION

Various embodiments for intelligent monitoring of a health state of a user while engaged in use of a computing device, are provided. In one embodiment, by way of example only, a method for intelligent monitoring of a health state of a user while engaged in use of a computing device, again by a processor, is provided. A health state of a user may be learned while engaged in one or more activities associated with a computing device. One or more mitigating actions may be identified and recommended to implement by the user to minimize one or more possible negative impacts upon the health state of the user while engaged in the one or more activities associated with the computing device.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
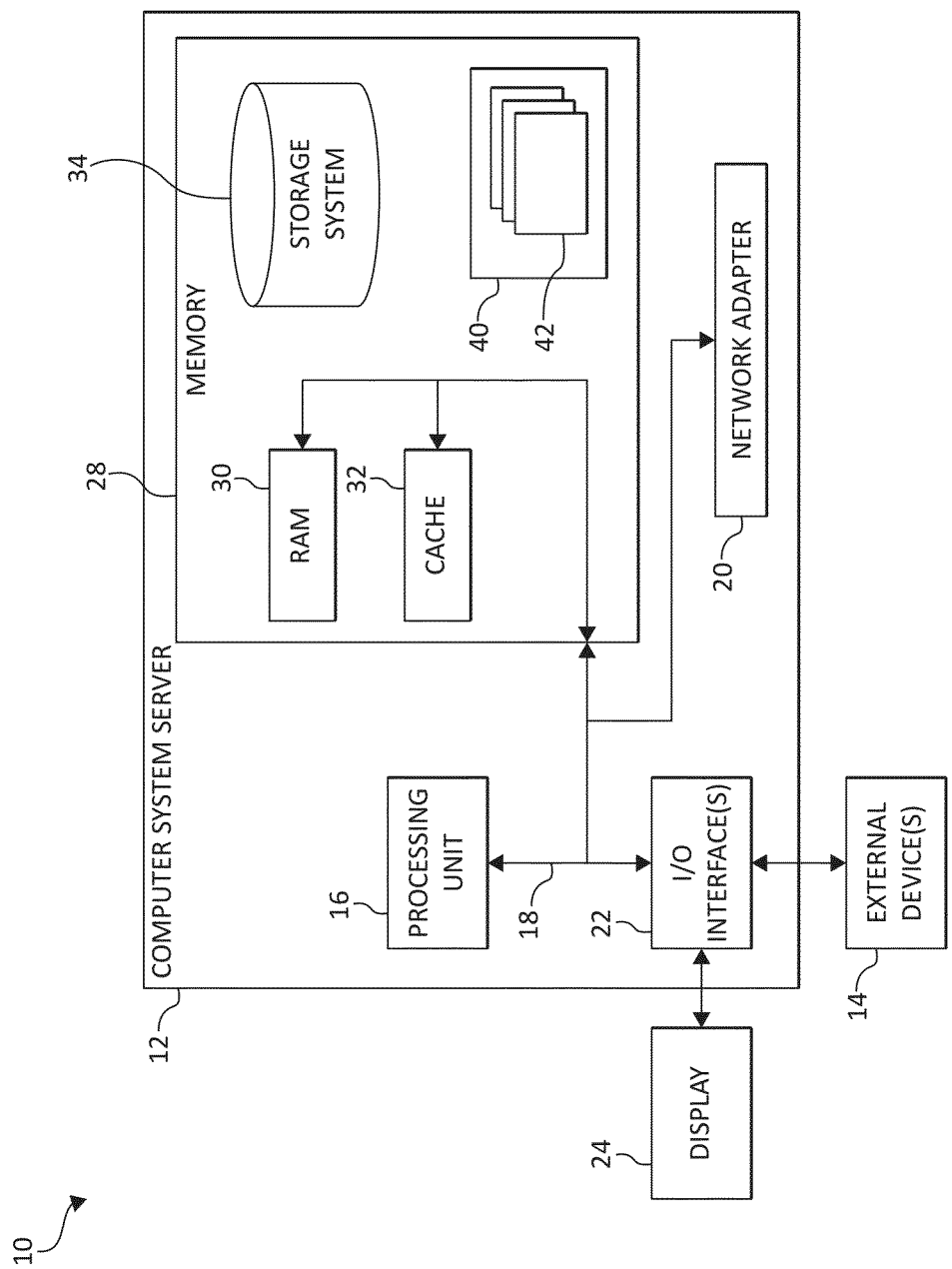
FIG. 1 is a block diagram depicting an exemplary computing node according to an embodiment of the present invention.

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices," which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user. For example, as the demand for and access to data continues to expand in society, consumers of information content, particularly individuals desiring to make well-informed decisions regarding a medical condition or health state, continue to increase. The openness of the internet with the ever-increasing availability of a variety of types of computing devices, IoT devices, and the cloud computing environment for viewing, interacting, or engaging with information, provides the ability of users to have continuous access to information content relating to a variety of settings. For example, there is a growing interest in personal health applications and recommender systems. However, current systems fall within one of the following categories: 1) devices and applications dedicated to only specific health condition or activities, (e.g., diabetes monitors, fitness trackers, etc.), 2) general companions that may assist users to diagnose their health conditions via dialogue, and/or 3) health recommender systems that recommend health products (e.g., medicine, reading material, etc.). These approaches do not provide a solution for intelligent monitoring of a health state of a user while engaged in operations/use of a computing device.

Accordingly, the present invention provides for intelligent monitoring of a health state of a user while engaged in use of a computing device by a processor. A health state of a user may be learned while engaged in one or more activities associated with a computing device. One or more mitigating actions may be identified and recommended to be implemented by the user to minimize one or more possible negative impacts upon the health state of the user while engaged in the one or more activities associated with the computing device. A health state of a user may be learned according to user behavior, physical conditions of the user, activities relating to computing activities (e.g., writing reports, working on a particular project, writing emails, claiming expenses, browsing the internet, watching a movie on a connected device such as tablet or smart TV, etc.) of the user, or a combination thereof.

In one aspect, the present invention provides a solution for learning and managing the health state of a computing device operator (e.g., user). In one aspect, the present invention may monitor activities of a user using/operating a computer. One or more parameters describing the health state of the computer user (e.g., stress, sleepiness/fatigue, etc.), using a device (e.g., wearable stress monitor), may be learned, identified, and/or modeled. The present invention may identify and learn the correlation between the health state of the user and the computer activities of the user and also context information such as, for example, a time of day, day of the week, luminosity, etc. The present invention may manage, adjust, and/or recommend one or more corrective/mitigating actions of the user during a defined time period (e.g., during the day) such as, for example, by attempting to maintain one of the parameters associated with the health state (e.g., stress level) below and/or above a defined threshold and/or avoiding peeks or long periods of stress. For example, when stress levels exceed a defined threshold, the present invention may suggest a mitigation action such as, for example, recommending to swap/change an order of tasks and recommend performing a less stressful task. That is, if a user's stress level as captured by one or more IoT devices (e.g., sensor or wearable sensors) is detected as rising and/or above a threshold level during the activity of writing emails in the morning, the recommendation may suggest to postpone writing emails until the end of the day (e.g., after 4:00 p.m.) and exchanging the email writing activity with getting up and walking around for 2 minutes and return to the computer to finish a project that the user enjoys (e.g., previously determined to be a less stressful activity where the stress of the user was below the defined threshold).

In one aspect, the present invention may take as additional input the user's calendar/schedule, including tasks to perform, required performance times, dependencies, and deadlines. This would enable rescheduling the user's tasks to avoid extended exposure to stress and stress peaks, while meeting the deadlines. For example, for a given user, the present invention may suggest avoiding stressful tasks close to deadlines.

In an additional aspect, the present invention may manage the health state of a user by learning the correlation between the user's activities and one or more parameters describing the health state of a user (as measured by an IoT device, an alternative computing device, and/or the computing device itself). The present invention may focus on a selected parameter (e.g., stress) as a measure of the user's health state. However, the present invention may not be restricted to merely one parameter (e.g., stress) but may user a combination of parameters representing each health state parameter, feature, or characteristic. For example, the health state parameters may include a variety of parameters such as, for example, fatigue, sleepiness, productivity, or other health related factors/parameters, etc. The health state of a user may be characterized by one or more measurable parameters such as, for example, the stress level of the user, sleepiness, fatigue/tiredness, emotional state/mood, etc. A health state parameter may be measured by a device (e.g., IoT device/sensor, computer, etc.) or provided directly by the user. Thus, the present invention not only provides mitigating/correcting activities (e.g., suggest break), but may also suggest rescheduling and swapping tasks as a way to balance the user's health state over a selected time period.

In an additional aspect, the present invention provides for learning and controlling the health state of a user interacting with a computer by managing the user's computer activities. In one aspect, the present invention may receive/us as input 1) user activity data, 2) context data, and/or 3) a user's health state data. In one aspect, the activity data may include, for example, heart rate and stress levels, fatigue, productivity measured as a function of typing speed, computer activity, etc.).

The present invention may provide/return as output, 1) suggestions for managing (e.g., rescheduling/swapping) tasks or activities so as to optimize, balance, and/or mitigate negative effects of the user's health state. In so doing, the present invention may perform one or more of the following steps. In step 1, the present invention may learn from the input data, one or more machine learning models of correlations between the user's health state and activities of the user in the context of external conditions (context data). In step 2, the present invention may monitor the user's activities, one or more parameters of the health state of the user, and/or external conditions. In step 3, the present invention may predict/project the user's health state depending on a current and planned activities, current health state data, and contextual information. In step 4, the present invention may, when extended periods of time and/or high peaks of stress are observed or predicted, plan/execute (task swapping or rescheduling) that optimizes, balances, and/or mitigates negative effects of the user's health state.

The present invention may be authorized to connect to one or more computers and/or IoT devices in the user's environment to collect and aggregate data for analysis (e.g., health state analysis). The data may be combined, aggregated, and/or shared to better monitor and mitigate the health state of the user across multiple environments (e.g., at work, at home, etc.).

It should be noted that as used herein, "user activity" may refer to activities of a user related to use of a computing device. "User health conditions" may be parameters that may indicate a presence/absence, type, and/or degree of a chronic or acute disease (e.g., diabetes, epilepsy, angina, etc.), symptom (e.g., headache, faint, etc.), history of medications/prescriptions, age, etc. A "user health state" may be a health state of an individual that may include the presence or absence of one or more conditions, symptoms or any particular variable which can help determine well-being. The user health state may include physical, mental, and/or social well-being. The user health state may include physical data that may be data quantifying or qualifying the physical conditions of a user such as, for example, amount of glucose, heart rate, skin temperature, etc. The user health state may include behavioral parameters that may be parameters characterizing the behavior of a user such as, for example, falling asleep, slow reaction time, posture, etc.

The user health state may include a user perception of comfort and/or discomfort such as, for example, perception of pain, fatigue, self-efficacy, etc. The user perception type of data may be provided by the user or detected via one or more computing devices/sensors. The user health state may be monitored using one of a plurality of types of device such as, for example an IoT device/sensor, computer, tablet, monitor, or other device that is an instrument (e.g., computing hardware and associated/embedded application/software) that monitors a user's physical conditions, such as a glucose monitoring watch, a heart rate monitor, a skin temperature sensor, a sleep monitor, etc. The contextual data may include an environment such as, for example, a place where a user's activity is taking place (e.g., business, vehicle, hospital, gym, outdoors, etc.). "Context" may refer to any information about external conditions related to the environment where the user is performing the activity (e.g., physical/virtual location data, time of the day, temperature, humidity, season, etc.).

In one aspect, cognitively reasoning and interacting may be performed with the user for collecting the feedback information, and the feedback information may be acquired using one or more IoT devices during the cognitive reasoning and interaction with the user.

A machine learning mechanism, employing one or more predictive models, may use the feedback information to learn the health state. In one aspect, the health state may include at least one or more medical conditions, a well-being (e.g., subjective well-being "SWB", emotional well-being, mental well-being, physical well-being, or an overall well-being) of the user, an emotional state of the user, biometric data, behavior patterns, a health profile of the user, or a combination thereof. In one aspect, well-being may be generally described as a normal/standardized or satisfactory condition of existence of the user or a state characterized by health, happiness, emotional stability, mental stability, physical stability, or success.

A well-being of a user may be defined. For example, a knowledge base or ontology may be used to define a well-being according to one or more parameters for a user and may include defining and/or indicating one or more correlations between a health state, a plurality of states, medical conditions, ADL, and context of daily living (CDL) and activities associated with a user operation a computing device. In an additional aspect, well-being may include the alleviation of adverse impacts upon a person's medical condition, emotional stability, mental stability, physical stability, financial stability, physiological problems, as well as to improve performance in many aspects of life such as daily activities, physical, emotional, mental activities, environmental conditions, and other functions, and also to contribute to the regulation of the various physiological systems of the organism (e.g., person) such as, the immune system. In one aspect, the well-being may be a SWB that may be defined as the degree to which people have positive thoughts and feelings about their lives and are often measured through self-reports of life satisfaction. A rating or scaling system may be used. For example, a number system from 1-10 may be used where 10 may indicate the greatest degree of positive thoughts and feelings while a 1 may indicate the least most degree of positive thoughts and feelings. A well-being of a person may be defined, stored, and/or included in a knowledge domain or ontology.

In one aspect, the one or more customized communications further include providing one or more notifications or suggestions to alter current activities of the user, future activities of the user, or a combination thereof while a user is operating a computing device. As used herein, activities of daily living ("ADL" or "ADLs") may refer to any activities that people perform during a day or other time period. For example, activities of daily living may include many activities such as, for example, writing reports, preparing presentation slides, programming in a computing programming language, working on a particular project or folder, using a particular operating system, application/software (e.g., infographics, design, project management, etc.), writing emails, claiming expenses, browsing the internet, watching a movie on a connected device such as tablet or smart TV, etc. The context of daily living ("CDL" or "CDLs") may refer to the context in which one or more ADLs are executed or carried out. The CDL may also include one or more dimensions such as, for example, time, location, environment conditions, weather conditions, and the like. A knowledge domain may provide one or more correlations or relationships between a person's health state and the ADLs and CDLs.

Some ADLs may also be applicable for one or more types of specific events/activities relating to operations of a computing device. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. The machine learning may provide a predictive model that may analyze, determine, identify, and/or predict any ADL behavior or activity for the user.

In one aspect, feedback information about the user using a computing device may be collected from the computing device itself or one or more IoT devices or sensors such as, for example, smart phones, wearable devices or sensors, biometric sensors, wearable sensors, and the like.). A stream of feedback data may be processed and the real-time flux of information enables the generation of knowledge or knowledge domain/ontology and enables the learning a health state of a user and generating personalized advice (e.g., suggestions, warnings, alerts, or recommendations) relating to the learned health state for adjusting one or more ADLs, CDLs, or other activities and environments while operating one or more computing devices that may negatively impact the person's well-being or state of health, using cloud computing and/or edge computing technology.

Also, as used herein, sensors may include biometric sensors, wearable sensors, computers, handheld devices (e.g., Global Positioning System "GPS" device or step counters), smart phones, and/or other sensor based devices.

Accordingly, the "health state" of a particular user may depend greatly upon contextual factors, such as a correlation or relationship between the health state and ADLs/CDLs of the user, and other contextual factors such as defined by a user or learned via artificial intelligence. A deeper, cognitive analysis of the health state of a person (e.g., a patient) may be learned based on, for example, standards, rules, practices, and/or learned ADLs, CDLs, and/or other related behaviors or activities. In short, a cognitive learning process using artificial intelligence may learn each of the actions, decisions, ADLs, CDLs, behavior patterns of a user, a medical profile (which may include data relating to medical care or medical conditions), or other activities. Each learned health state may be saved as part of a user profile and/or retained in a knowledge domain. For example, the cognitive learning may learn preferred ADLs for particular priorities, preferences, or even time periods.

The ontology may include, but is not limited to, the knowledge domain or data repository of a collection of material, information, content and/or other resources related to a particular subject or subjects. For example, the ontology may include, data relating to a user's health state. The ontology may have defined ADLs, CDLs, and a user profile (e.g., calendar information, historical data relating to medical conditions of the user, emotional/physical/mental condition of the user, preferences, priorities, biomedical data, psychophysical parameters of the user, medical history, emotional data, skills set, and the like). The ontology may also have environmental data, medical conditions, time of the day, day of the week, weather data, and the like.

One or more machine learning models may be invoked and applied to cognitive learning about the user and/or a health state of the user while operating one or more computing devices such as, for example, ADLs, CDLs, priorities, activity preferences, daily or future calendaring, behaviors, skill sets of a user, medical conditions, capabilities, performance capabilities, and/or other types of data needed for providing communications to suggest one or more alterations, adjustments, or planning alternative activities relating to operating a computing device to eliminate or reduce possible adverse impacts on the person's health state.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
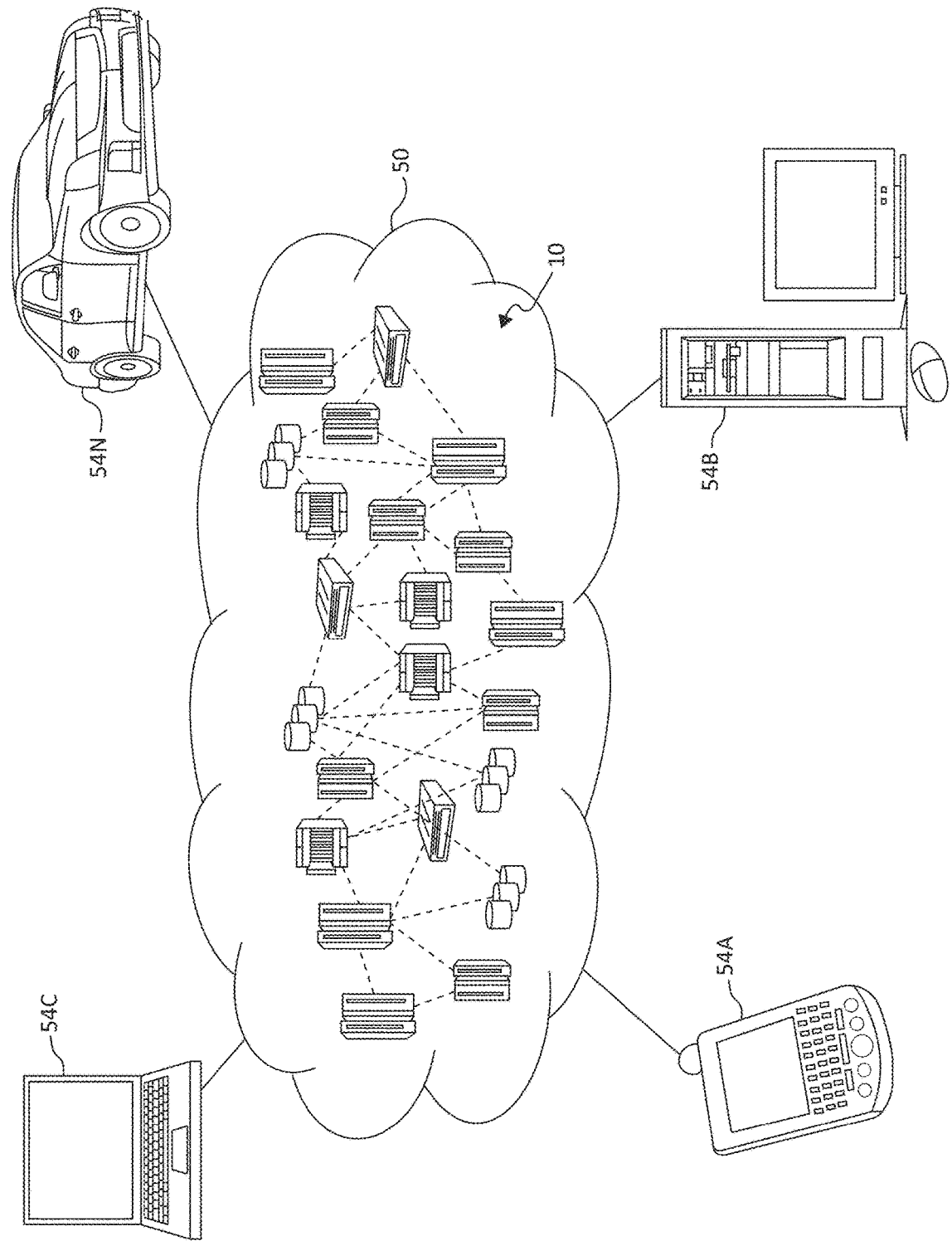
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
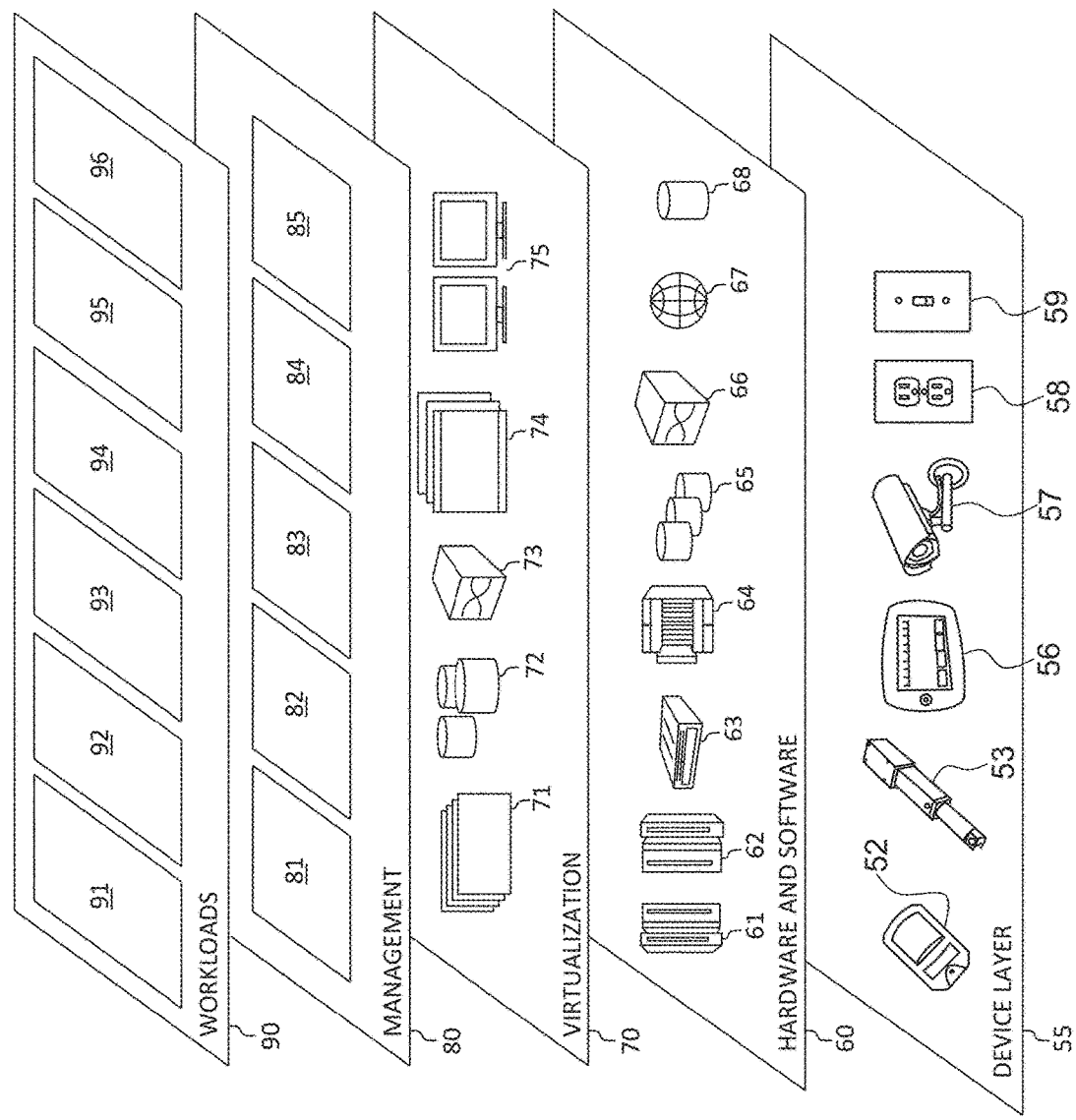
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent monitoring of a health state of a user while engaged in operation of a computing device. In addition, workloads and functions 96 for intelligent monitoring of a health state of a user while engaged in operation of a computing device may include such operations as data analytics, data analysis, and as will be further described, notification functionality. One of ordinary skill in the art will appreciate that the workloads and functions 96 for intelligent monitoring of a health state of a user while engaged in operation of a computing device may also work in conjunction with other portions of the various abstraction layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for providing intelligent monitoring of a health state of a user while engaged in operation of a computing device in a computing environment. The present invention may monitor one or more activities of a user using/operating one or more computers and one or more parameters describing the health state of the computer user (e.g., stress) using a device (e.g., an IoT device such as, for example, a wearable stress monitor).

The present invention may identify and learn the correlation between the health state of the user and the computer activities of the user along with contextual information such as, for example, a time of day, day of the week, luminosity, etc. The present invention may manage/control, adjust, influence, and/or monitor the health state of the user throughout a selected time period such as, for example, by keeping/maintaining one or more parameters representing a characteristic, feature, or property of the health state of the user (e.g., a stress level) below, above, and/or equal to a defined threshold (depending on the parameter) to avoid defined/extended periods/peeks of exposure of the one or more parameters to the user (e.g., reduce exposure of stress to the user). For example, when stress levels exceed a threshold, the present invention may recommend and/or suggest a mitigation action such as, for example, swapping an order of tasks and performing a less stressful task while postponing a task/activity detected as causing negative impact to the health state of the user to an alternative time period (or even recommending to terminate/cancel the activity altogether). The present invention may take as additional input the user's calendar/schedule, including the tasks to perform, required times, dependencies, and deadlines. This would allow the present invention to reschedule the user's tasks to avoid extended exposure to stress and stress peaks, while meeting the deadlines. For example, the present invention may suggest avoiding stressful tasks close to deadlines for the user.

Figure 4:
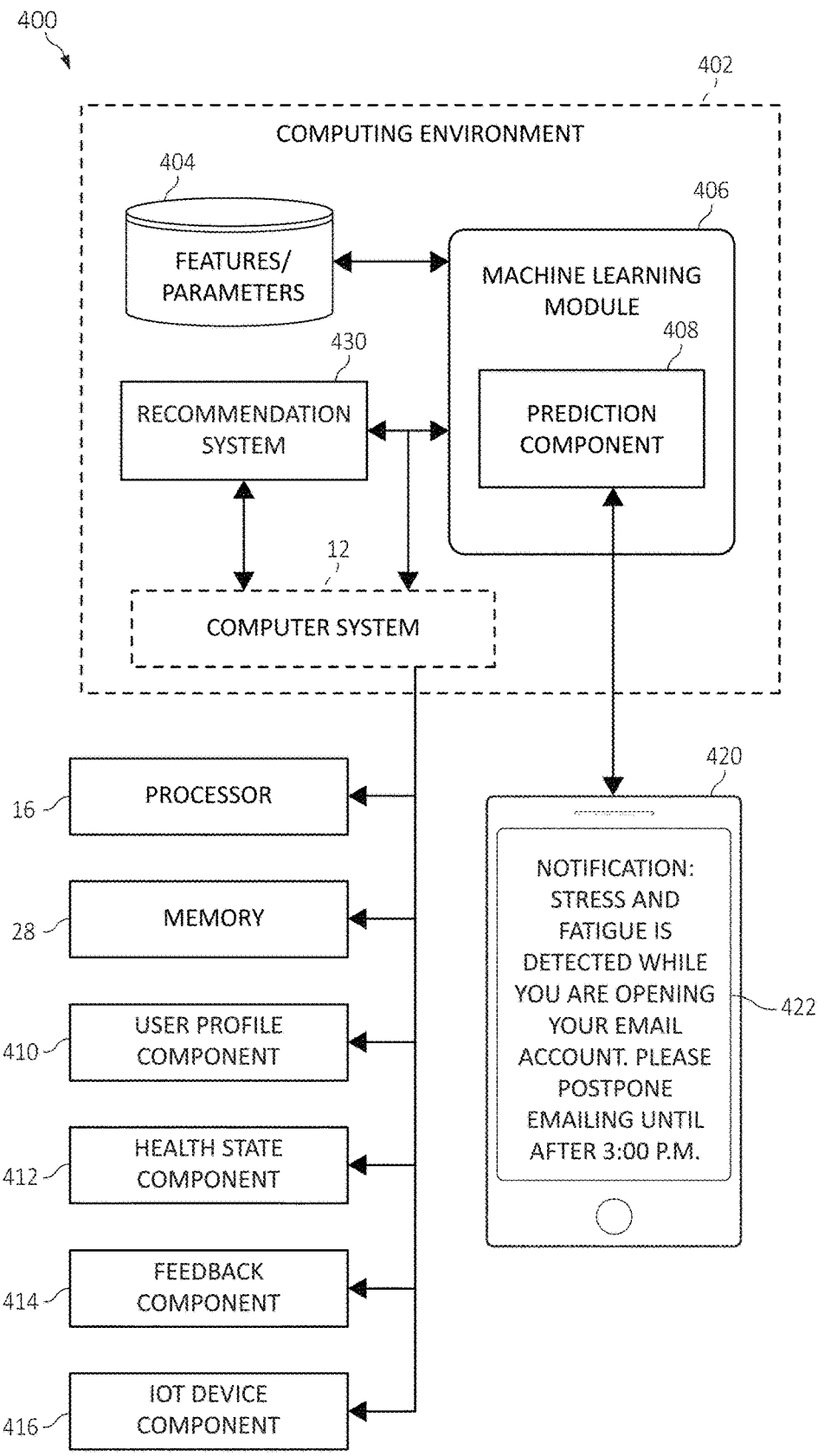
FIG. 4 is a diagram depicting various user hardware and computing components functioning in accordance with aspects of the present invention.

Turning now to FIG. 4, a block diagram depicting exemplary functional components 400 according to various mechanisms of the illustrated embodiments is shown. FIG. 4 illustrates intelligent monitoring of a health state of a user while engaged in operation of a computing device in a computing environment, such as a computing environment 402, according to an example of the present technology. As will be seen, many of the functional blocks may also be considered "modules" or "components" of functionality, in the same descriptive sense as has been previously described in FIGS. 1-3. With the foregoing in mind, the module/ component blocks 400 may also be incorporated into various hardware and software components of a system for intelligent monitoring of a health state of a user while engaged in operation of a computing device in accordance with the present invention. Many of the functional blocks 400 may execute as background processes on various components, either in distributed computing components, or on the user device, or elsewhere. Computer system/server 12 is again shown, incorporating processing unit 16 and memory 28 to perform various computational, data processing and other functionality in accordance with various aspects of the present invention.

The system 400 may include the computing environment 402, a recommendation system 430, and a user equipment ("UE") 420, such as a desktop computer, laptop computer, tablet, smart phone, and/or another electronic device that may have one or more processors and memory. The UE 420, the recommendation system 430, and the computing environment 402 may each be associated with and/or in communication with each other, by one or more communication methods, such as a computing network.

In one example, the UE 420 and/or the recommendation system 430 may be controlled by a user associated with the computing environment 402. In one aspect, one or more components of computing environment 402 may be internal to the UE 420. In an alternative embodiment, one or more components of the computing environment 402 may be external to the UE 420.

In one aspect, the computing environment 402 may provide virtualized computing services (i.e., virtualized computing, virtualized storage, virtualized networking, etc.) to devices such as, for example, UE 420. More specifically, the computing environment 402 may provide virtualized computing, virtualized storage, virtualized networking and other virtualized services that are executing on a hardware substrate.

As depicted in FIG. 4, the computing environment 402 may include a machine learning module 406, features and/or parameters 404 that are associated with a machine learning module 406, and the recommendation system 430. The features and/or parameters may include ADLs, CDLs, health state data, and a knowledge domain/ontology. The features and/or parameters database 404 may also include user profiles (e.g., a collection of user profiles with various information relating to the health state of each user) for the recommendation system 430 and/or IoT devices associated with an IoT device component 416 (e.g., an IoT sensor device, camera, voice activated device, and other types of IoT devices).

It should be noted that one or more IoT devices may be represented as the IoT device component 416 may be coupled to the recommendation system 430. The features and/or parameters 404 may be a combination of ADLs, CDLs, features, parameters, rules, behavior characteristics, biometric data, user profile data, calendaring data, health data, physical or mental capabilities, emotional data, medical condition data, health constraint data, historical data, tested and validated data, or other specified/defined data for testing, monitoring, validating, detecting, learning, analyzing and/or calculating various conditions or diagnostics relating to cognitively learning the health state of a user for identifying and recommending via the recommendation system 430 one or more mitigating actions to implement by the user to minimize one or more possible negative impacts upon the health state of the user while engaged in the one or more activities associated with the UE 420.

That is, different combinations of ADLs, CDLs, features, or parameters may be identified, learned, detected (via the IoT device component 416 or device 420), and/or applied to the input data for learning or training one or more machine learning models of the machine learning module 406. The features and/or parameters 404 may define one or more settings of an IoT device (e.g., UE 420) associated with the IoT device component 416 to enable the UE 420 to interact with the UE 420 and the computer system 12. The IoT device component 416 may be associated with the recommendation system 430 and the UE 420. In one aspect, the IoT device component 416 may be included in and/or associated with the UE 420.

The computing environment 402 may also include the computer system 12, as depicted in FIG. 1. The computer system 12 may also include the user profile component 410, a health state component 412, a feedback component 414, and the IoT device component 416 each associated with the machine learning module for identifying, learning, applying, and/or training one or more machine learning models and also for applying multiple combinations of parameters that represent the health state of the user such as, for example, ADLs, CDLs, features, parameters, behavior patterns or characteristics, patient/user profile data, historical data, or a combination thereof to the machine learning model for use in the recommendation system 430 for cognitively learning a health state of a user and for identifying and recommending via the recommendation system 430 one or more mitigating actions to implement by the user to minimize one or more possible negative impacts upon the health state of the user while engaged in the one or more activities associated with the UE 420.

In one aspect, the machine learning module 406, which may be associated with the recommendation system 430, may include a prediction component 408 for cognitively learning a health state of a user and recommending personalized advice, suggestions, or notifications of a user profile to minimize one or more possible negative impacts upon the health state of the user and/or to avoid adverse impacts on the user's health state, by one or more IoT devices 420 associated with the IoT device component 416 in the recommendation system 430.

The user profile component 410 may include data (e.g., historical data and/or real-time data) relating to a health state of a user (e.g., the well-being of the user), ADLs, CDLs, behavioral patterns and characteristics, biometric data, medial history data, contextual data, feedback information, and data associated with the knowledge domain/ontology.

The computer system 12 may use the user profile component 410 and/or the IoT device component 416 to cognitively determine the level of the well-being or health state of the user according to user behavior, physical conditions of the user, ADLs and associated CDLs of the user, or a combination thereof. The user profile component 410 may collect, gather, calculate, and cognitively determine the well-being/health state. The user profile component 410 may monitor the health state of the user using the one or more applications of a computing device, one or more application components of a computing device, one or more IoT devices, or a combination thereof. The user profile component 410 may also cognitively determine the well-being/health state while a user is engaged in one or more activities associated with the UE 420.

The health state component 412 may monitor the health state of the user and the one or more activities of the user associated with the UE 420. The health state component 412, in association with the machine learning module 406, may learn the health state of a user according to user behavior, contextual information, physical conditions of the user, activities of daily living (ADL) and associated context of daily living (CDL) of the user, or a combination thereof. The health state component 412, in association with the machine learning module 406, may identify those of the one or more activities that negatively impacts the health state of the user.

The prediction component 408, in association with the machine learning module 406 and the health state component 412, may predict the health state of the user according to the one or more activities to identify the one or more health state risks.

Also, the recommendation system 430 may recommend one or more mitigating actions (or corrective actions) to implement by the user to minimize one or more possible negative impacts upon the health state of the user while engaged in the one or more activities associated with the UE 420. The recommendation system 430 may suggest implementation of one or more mitigating actions at one or more time periods, upon occurrence of one or more events or activities causing one or more parameters of the health state of a user to exceed or fall below a defined threshold, or upon detection of one or more physical parameters of the user collected by the IoT device component 416 (e.g., one or more IoT devices, sensor devices, etc.) the UE 420, or combination thereof exceeding and/or falling below a defined threshold.

A feedback component 414 may use a variety of feedback information relating to the recommendation system 430 and feedback information pertaining to the user may be stored and maintained in the feedback component 414 and used by the machine learning module 406, the features and/or parameters 404, or both. The feedback component 414 may collect a variety of feedback information for the user relating to the health state and the recommended mitigating suggestions. For example, the feedback component 414 may collect data gathered from the user (e.g., cognitive interaction and reasoning), the UE 420, the IoT device component 416 or other source for learning the health state of a user, contextual information, or combination thereof.

The machine learning module 406, in association with the feedback component 414, may collect the feedback, learn the one or more application components, the IoT devices, or a combination thereof suitable to users depending on their health conditions, activities, and environments.

Also, the UE 420 may include a graphical user interface (GUI) 422 enabled to display on the UE 420 one or more user interface controls for a user to interact with the GUI 422. For example, the GUI 422 may display one or more customized communications to a user to alter one or more activities of the user so as to avoid one or more possible negative impacts upon the health state of the user via an interactive graphical user interface (GUI). That is, the GUI 422 may display identified and recommended applications, application components, IoT devices, or a combination thereof to minimize one or more possible negative impacts upon the health state of the user. The GUI 422 may display one or more mitigating actions to avoid one or more possible negative impacts upon the health state of the user according to the aggregated data.

For example, the one or more customized communications may indicate or display audibly and/or visually on the GUI 422 "Notification: Stress and Fatigue is detected while you are opening your email account. Please postpone emailing until after 3:00 p.m." The message notification on the GUI 422 may vary, change, and be updated according to real time feedback received from the feedback component 414. Also, the message notification on the GUI 422 may be a series of interactive messages between a user of the UE 420 and the computing environment 402.

In one aspect, the machine learning module 406 may cognitively learn a health state of a user while operating the UE 420. The estimation/predictive modeling (or machine learning modeling), as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the computing system 12/computing environment 402 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Figure 5:
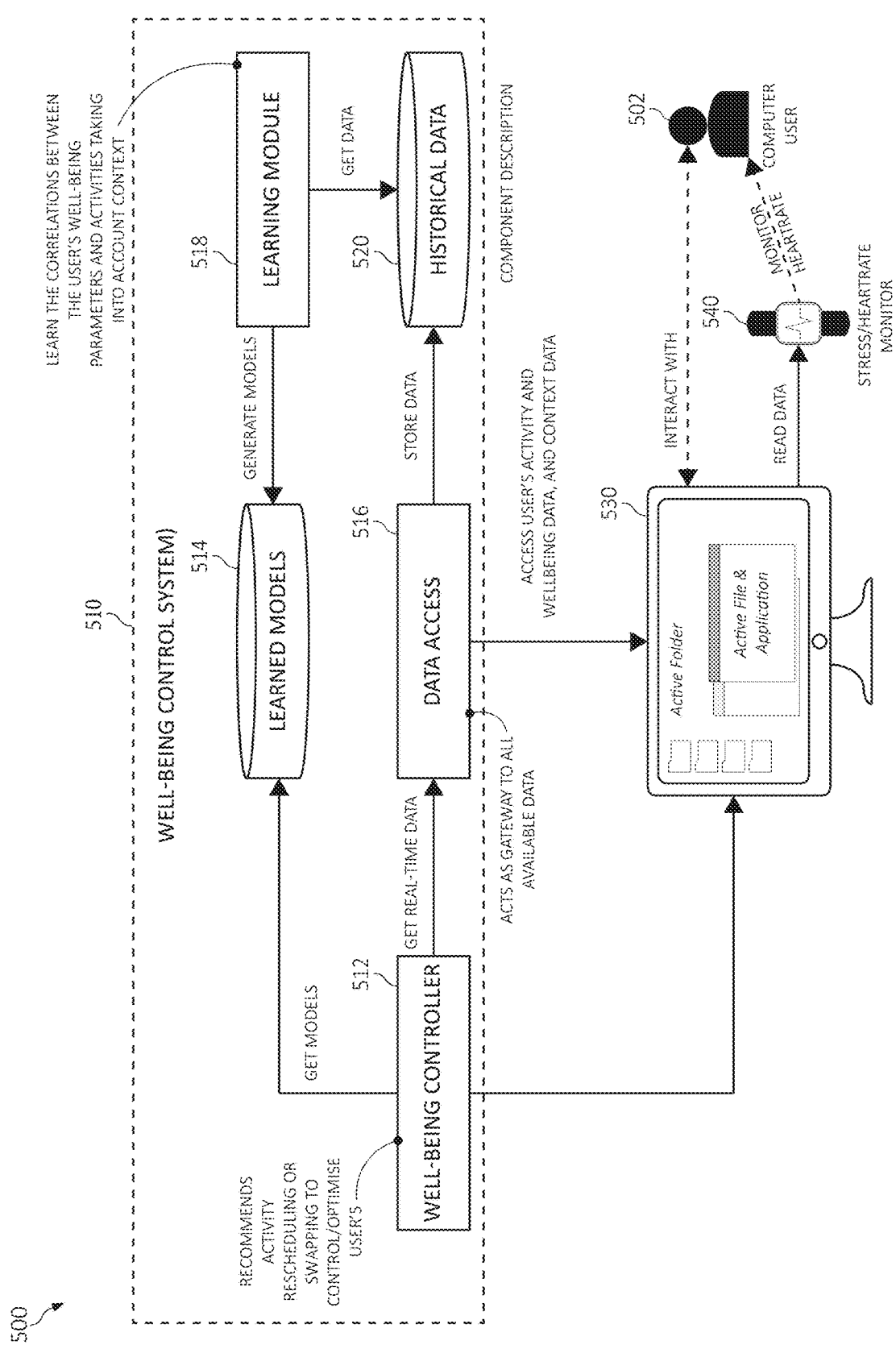
FIG. 5 is an additional block diagram depicting an exemplary functional relationship between various aspects of the present invention.

Turning now to FIG. 5, a block diagram of an exemplary functionality 500 of an intelligent health state monitoring system 510 (e.g., "well-being control system") architecture is depicted. It should be noted that the intelligent health state monitoring service/assistant system 510 may be included in and/or associated with computer system/server 12 of FIG. 1, incorporating one or more processing unit(s) 16 to perform various computational, data processing and other functionality in accordance with various aspects of the present invention.

As shown, the various blocks of functionality are depicted with arrows designating the blocks' 500 relationships with each other and to show process flow of the intelligent health state monitoring service/assistant system 510. Additionally, descriptive information is also seen relating each of the functional blocks 500. As will be seen, many of the functional blocks may also be considered "modules" or "components" of functionality, in the same descriptive sense as has been previously described in FIGS. 1-4. With the foregoing in mind, the module blocks 500 may also be incorporated into various hardware and software components of a system for implementing an intelligent health state monitoring service/assistant in accordance with the present invention. Many of the functional blocks 500 may execute as background processes on various components, either in distributed computing components, or on the user device, or elsewhere, and generally unaware to the user performing generalized tasks of the present invention.

As illustrated in FIG. 5, intelligent health state monitoring system 510 may include a well-being controller 512 (e.g., health state controller), one or more learned models 514, a learning module 518, historical data 520, and data access component 516 (e.g., "data access"), each of which may be in association with computer 530.

The computer 530 may be in communication, interaction, and/or association with user 502 and a device 540, which may be a stress/heartrate monitor device or other IoT computing device/sensor. The computer 530 may receive (e.g., read data) from the device 540 such as, for example, stress data and/or heart rate.

In one aspect, the well-being controller 512 may recommend one or more activities be rescheduled and/or swapped with other activities to control/optimize a health state (e.g., well-being) of the user 502. The well-being controller 512 may be used for recommending activity plans that optimize, balance, and/or mitigate negative effects of the user's health state. In so doing, the well-being controller 512 may gather/received data (e.g., real-time data) from 530 via a data access component 516. That is, the data access component 516 may be used for collecting and providing access to input data for the intelligent health state monitoring system 510.

In one aspect, the recommended/suggested activities may include, for example, postponing a current task until another time period, rescheduling or swapping two or more tasks, and/or suggesting alternative tasks better suited to a current user health status (e.g., in case of fatigue the recommended/suggested activities may include easy tasks or taking a break).

In an additional aspect, the well-being controller 512 may provide one or more recommendations/suggestions intended, designed, and generated/created to manage the user's health state by minimizing periods of discomfort (e.g., reduce stress over a defined time period), avoiding peaks of discomfort (e.g., stress), and spreading the negative health state parameters/discomfort to the user over a selected time period (e.g., throughout a day, or pushing an activity causing a negative effect to the health state of the user towards the end of the day, etc.).

Additionally, the well-being controller 512 may generate one or more reports on the health state of one or more members of a team/group and what effects influence each of the members of a team/group, types of tasks that are most suitable to each member, and/or recommendations as to how to best manage/assign team tasks to individuals.

In an additional aspect, the well-being controller 512 may identify and/or learn an optimized/best policy to maximize a user's health state over a time period/horizon (e.g., one working day/week), based on a Markov decision processes ("MDP") and reinforcement learning operations.

The well-being controller 512 may also receive feedback on each recommendations from the user either explicitly (e.g., rating/ranking of recommendations) or implicitly (e.g., user ignoring recommendations) to learn improved future recommendations. Thus, the well-being controller 512 may not only suggest various recommendations such as, for example, swapping of activities or taking a break, but also monitoring activity data of the user and suggest actions on the order/schedule of the activities themselves.

The accessed data may be stored as historical data 520. The learning module 518 may retrieve the historical data 520 and learn correlations between the user's health state parameters and activities associated with interacting with the computer 530 while considering and taking into account the contextual data while using the computer 530. That is, the learning module 518 may be used to learn models of correlation between the parameters of the user's health state and activities while also considering contextual data. In one aspect, the contextual data may be obtained from one or more alternative devices such as, for example, digital assistant (PDA) or cellular telephone 54A, desktop computer 54B, laptop computer 54C, and/or automobile computer system 54N of FIG. 2 or other external computing device. In one aspect, the contextual data may include, for example, temporal data (e.g., time of day, day of week, time of year, etc.), environmental context data (e.g., luminosity, temperature, physical/virtual location of a user), project information (e.g., proximity to project deadlines and/or time lines), and/or task schedules, dependencies, and/or selected deadlines associated with the user (e.g., work deadlines).

The learning module 518 may generate one or more learned models 514, which may be retrieved by the well-being controller 512 for recommending mitigating activities (e.g., rescheduling or swapping activities of the user 502 while interacting with computer 530). In one aspect, the learned models 514 may include, for example, a correlation between the activity data and user's health state while taking into account context information. The learned models 514 may include models that support a prediction the user's health state depending on the user's current activity and previous activities, current well-being data, and context information.

More specifically, in a training phase, the intelligent health state monitoring system 510 may monitor a sequence of activities of user 502 while interacting with computer 530. The device 540 may also be used for monitoring the health state of the user 502 while the user 502 is performing the sequence of activities of user 502 while interacting with computer 530. The intelligent health state monitoring system 510 may categorize the activities according to a combination of the following criteria (e.g., active applications, active folders, file types, file/locations, activity types, etc.).

That is, the activities may be categorized according to the following criteria. 1) A type of application used such as, for example, an email client, text editor, an internet/web browser, a financial application/expense tool, a calendaring application, time reporting, etc. 2) A folder such as, for example, a project folder in which one or more files used by a user are saved. 3) A file type such as, for example, a type of file being used by a user (e.g., a presentation file, a spreadsheet file, a word processing file, a document preparation file, a unified modeling language diagram, a type of computing programming language, etc.) 4) A specific file a user is working on such as, for example, specific report document, etc. 5) A type of task to which a user's activity while using a computer is related (e.g., a web-based hosting service for version control issue, calendar entry, etc.), which may be provided by the user. 6) Context and external conditions may also be categories such as, for example, a day of the week, a time of day, luminosity (e.g., an amount of energy emitted per unit of time), proximity to deadlines on a user's calendar, etc.

In one aspect, the intelligent health state monitoring system 510 may correlate user wellbeing data (e.g., stress level data) received from the device 530 (e.g., an IoT device such as, for example, a smart watch). The intelligent health state monitoring system 510 may correlate the wellbeing (e.g., stress levels) of the user 502 with other inputs such as, for example, activities of the user and contextual data.

Using one or more machine learning operations (e.g., K-nearest neighbors algorithm "KNN", deep learning, etc.) to learn the non-linear mapping between the vectors of activities and the user's health state parameters. For example, the intelligent health state monitoring system 510 may identify and learn that a stress level of a user exceeds a defined threshold on a selected period of time (e.g., a user is stressed on Monday mornings). The intelligent health state monitoring system 510 may identify and learn that administrative and communication tasks such as, for example, determining financial expenses, writing emails, and report writing are the most stressful tasks for a user compared to other activities/tasks performed by the user while interacting with a computing device (e.g., device 530). The intelligent health state monitoring system 510 may identify and learn that starting a day with an administrative task is correlated with a parameter of the health state exceeding a defined threshold for a selected period (e.g., stress levels increase throughout the whole day). Also, the intelligent health state monitoring system 510 may identify and learn that other activities such as, for example, computing programming tasks are associated with parameters associated with a health state that mitigate any effects of negative health state (e.g., computer programming lowers the user's stress levels). Alternatively, the intelligent health state monitoring system 510 may identify and learn that other activities such as, for example, alternating activities between computing programming and administrative/reporting tasks may be associated with increasing the negative health state of a user over a selected time period (e.g., increase a stress level of the user throughout the day. The intelligent health state monitoring system 510 may identify and learn that activities such as, for example, computing working on files inside a selected folder of a user (e.g., "My_Personal_Project" folder) is more stressful than working on other files inside another folder (e.g., "My_Work_Project" folder). The intelligent health state monitoring system 510 may identify and learn that activities such as, for example, working on a first type of computer programming files with is less stressful than working on a second type of computer programming files).

To further illustrate, consider the following example using components of intelligent health state monitoring system 510. Assume a user starts working on Monday at 8:00 a.m. in the morning. As the user's first task, the user interacts with a computing device and opens "My_Personal_Project" folder, then opens the file "deliverables." The user then starts working on "My_Work_Project" document. As a first task on a Monday and the user begins to feel stressed based on contextual data (e.g., various environmental factors). Also, an application being operated by the user begins to underperform causing increased stress, but the user attempts to continue working on the "My_Work_Project" document using the faulty application. After a selected period of time (e.g., one hour), the user is experiencing additional levels of stress based on both the contextual data (e.g., contextual data that may include air temperature, humidity, time, season, noise, etc.) and, also, without cognitive awareness, the user starts pressing on various components of the computer (e.g., keyboard or mouse pad) with a greater amount of force than as compared to other times of lower stress. A smart watch located on the user's person is now reporting to the computer of the user high levels of stress. The intelligent health state monitoring system 510 associated with the user's computer identifies and learns that the user has been exposed to a high level of stress (e.g., stress greater than a learned and defined threshold parameter) for a selected/defined period of time. According to an analysis operation performed by the intelligent health state monitoring system 510, the intelligent health state monitoring system 510 may learn that the user is more stressed on Monday mornings as compared to other work days. Also, the intelligent health state monitoring system 510 learns that the stress level of the user is also increased when working on "My_Work_Project" using a word processing system that may be faulty or may not be easy/comfortable to use.

Accordingly, the intelligent health state monitoring system 510 accesses the user's calendar schedule and identifies one or more deadlines associated with work requirements contained in a folder or web-based hosting service for versioning control that may identify files, repositories, and applications the user has been working on/with recently. The intelligent health state monitoring system 510 may recommend/suggest that the user should consider working on a less stressful task such as, for example, swapping out and fixing one or more computer bugs in a computing program that were assigned to the user in the web-based hosting service for versioning control and that are due by Wednesday and Thursday. Thus, the activity of working on "My_Work_Project" may be delayed and swapped since the intelligent health state monitoring system 510 learns and identifies the work report is not due until the end of the month. The intelligent health state monitoring system 510 may also suggests the user should return to "My_Work_Project" later in the afternoon.

Figure 6:
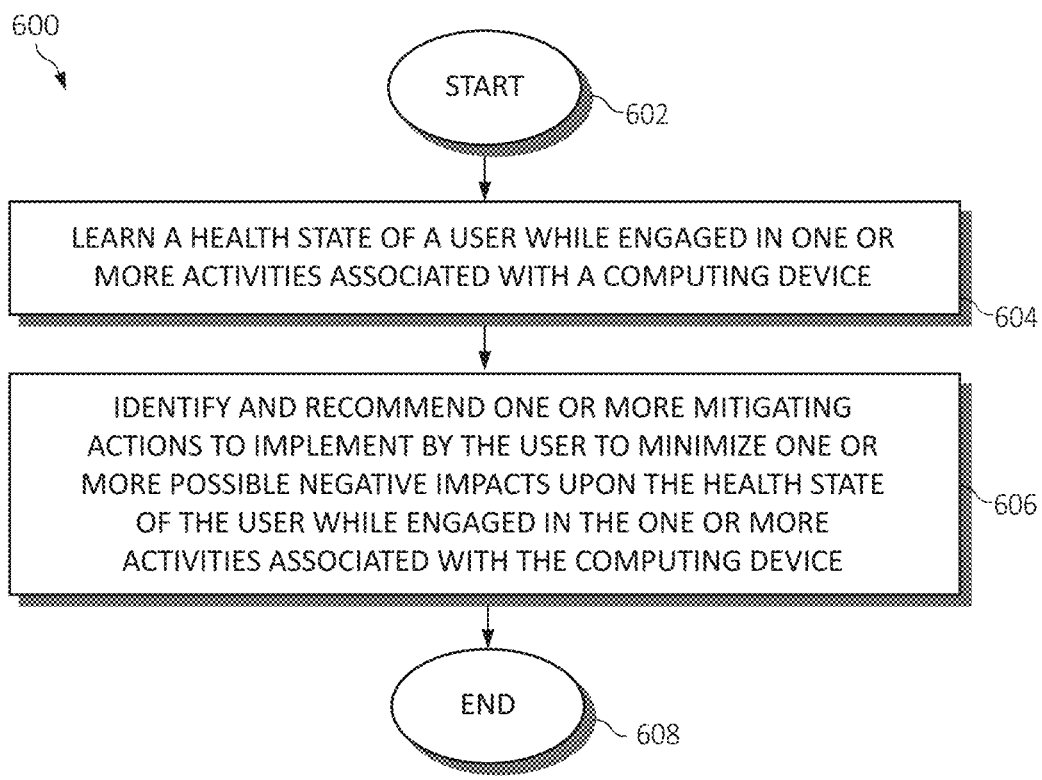
FIG. 6 is a flowchart diagram depicting an exemplary method for intelligent monitoring of a health state of a user while engaged in use of a computing device by a processor, again in which aspects of the present invention may be realized.

Turning now to FIG. 6, a method 600 for intelligent monitoring of a health state of a user by a processor is depicted, in which various aspects of the illustrated embodiments may be implemented. The functionality 600 may be implemented as a method executed as instructions on a machine, where the instructions are included on at least one computer readable medium or one non-transitory machine-readable storage medium. The functionality 600 may start in block 602.

A health state of a user may be learned while engaged in one or more activities associated with a computing device, as in block 604. One or more mitigating actions may be identified and recommended to implement by the user to minimize one or more possible (e.g., probable or potential) negative impacts upon the health state of the user while engaged in the one or more activities associated with the computing device, as in block 606. The functionality 600 may end, as in block 608.

Figure 7:
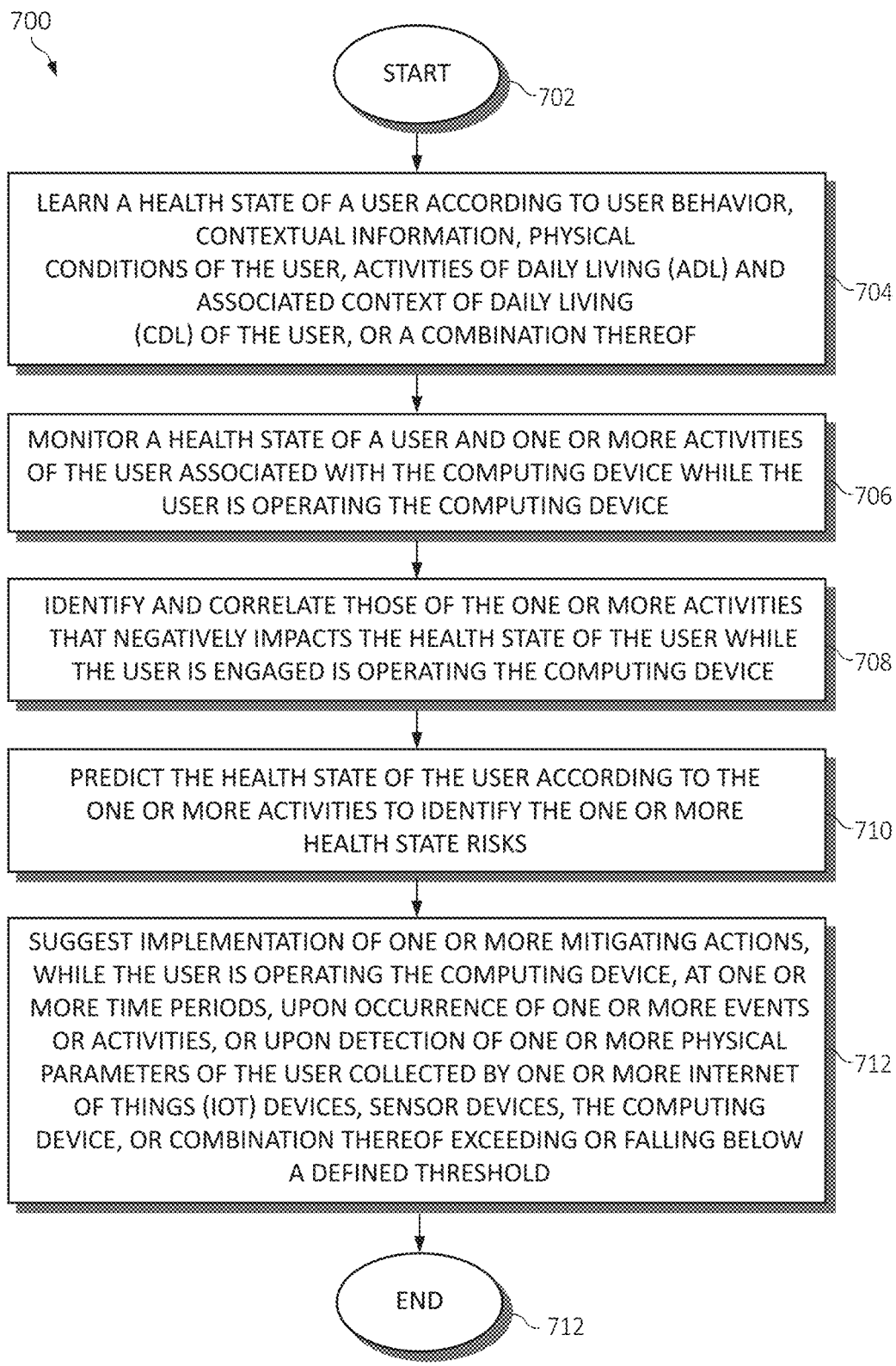
FIG. 7 is an additional flowchart diagram depicting an exemplary method for intelligent monitoring of a health state of a user while engaged in use of a computing device by a processor, again in which aspects of the present invention may be realized.

Turning now to FIG. 7, a method 700 for intelligent monitoring of a health state of a user by a processor is depicted, in which various aspects of the illustrated embodiments may be implemented. The functionality 700 may be implemented as a method executed as instructions on a machine, where the instructions are included on at least one computer readable medium or one non-transitory machine-readable storage medium. The functionality 700 may start in block 702.

A health state of a user may be learned according to user behavior, contextual information, physical conditions of the user, activities of daily living (ADL) and associated context of daily living (CDL) of the user, or a combination thereof, as in block 704. The health state of the user and the one or more activities of the user associated with the computing device may be monitored while the user is operating the computing device, as in block 706. Those of the one or more activities may be identified and correlated (the health state) that negatively impacts the health state of the user while the user is engaged is operating the computing, as in block 708. The health state of the user may be predicted according to the one or more activities to identify one or more health state risks, as in block 710. One or more mitigating actions, while the user is operating the computing device, may be suggested for implementation at one or more time periods, upon occurrence of one or more events or activities, or upon detection of one or more physical parameters of the user collected by one or more IoT devices, sensor devices, the computing device, or combination thereof exceeding or falling below a defined threshold, as in block 712. The functionality 700 may end, as in block 714.

In one aspect, in conjunction with and/or as part of at least one block of FIGS. 6-7, the operations of methods 600 and/or 700 may include each of the following. The operations of methods 600 and/or 700 may activate, deactivate, or configure one or more applications, one or more application components, one or more internet of things (IoT) devices, or a combination thereof to monitor the health state of the user. The operations of method 700 may monitor the health state of the user using the one or more applications, the one or more application components, the one or more IoT devices, the computing device or a combination thereof. The operations of method 700 may recommend one or more mitigating actions to avoid one or more possible negative impacts upon the health state of the user according to the collected data from the one or more application components, the one or more IoT devices, or a combination thereof.

The operations of method 700 may initialize a machine learning mechanism to collect feedback, learn the one or more mitigating actions for the user, learning one or more health conditions, activity, scheduling data, contextual data, and a current environment of the user. That is, the machine learning mechanism may be initialized to collect feedback, learn the health state of the user, learn one or more mitigating actions, or a combination thereof. The health state includes at least one or more medical conditions, a subjective well-being (SWB) of the user, an emotional state of the user, biometric data, behavior patterns, a health profile of the user, or a combination thereof.

Moreover, the operations of method 700 may implement a set of rules for using a learned model. The feedback information, a health state profile of the user, one or more ADLs of the user, CDLs, or a combination thereof may be used in the learned model. The user feedback may also be augmented with information from a domain knowledge that describes correlations between the health state, ADL, CDL, or a combination thereof with various activities associated with use of a computing device by the user.

The operations of method 700 may generate one or more reports on the health state of one or more user of a team, group, or organization and what affects each user's health state, what types of tasks are most suitable for each user, and recommendations as to how to manage/assign team tasks to one or more user. Also, feedback may be received and/or provided on recommendations from the user either explicitly (e.g., rating/ranking of recommendations) or implicitly (e.g., user ignoring system recommendation) to learn improved future recommendations.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for implementing an intelligent monitoring of a health state of a user in a computing environment by a processor, comprising:
   receiving health data of the user collected by one or more computing devices in one or more environments;
   receiving user activity data of one or more activities performed by the user on the one or more computing devices in the one or more environments;
   executing machine learning logic to learn the health state of the user while engaged in the one or more activities associated with the one or more computing devices in the one or more environments by generating a health model trained to correlate the health data to the user activity data, wherein the health model correlates specific sequences of the one or more activities performed by the user on the one or more computing devices at specific times to specific health events impacting the health state of the user;
   identifying and recommending one or more mitigating actions to implement by the user to minimize one or more possible negative impacts upon the health state of the user while engaged in the one or more activities associated with the one or more computing devices;
   receiving user feedback, as feedback data, with respect to an effectiveness of the one or more mitigating actions implemented by the user; and
   executing the machine learning logic to re-train the health model using the feedback data to iteratively optimize the health model to enhance the effectiveness of future mitigating actions recommended be implemented by the user.

2. The method of claim 1, further including monitoring the health state of the user, the one or more activities of the user associated with the one or more computing devices, the one or more environments, one or more contextual parameters, or a combination thereof.

3. The method of claim 1, further including learning the health state of the user according to user behavior, contextual information, physical conditions of the user, or a combination thereof.

4. The method of claim 1, further including identifying those of the one or more activities that negatively impacts the health state of the user.

5. The method of claim 1, further including predicting the health state of the user according to the one or more activities to identify the one or more health state risks.

6. The method of claim 1, further including suggesting implementation of the one or more mitigating actions at one or more time periods, upon occurrence of one or more events or activities, or upon detection of one or more physical parameters of the user collected by one or more internet of things (IoT) devices, sensor devices, the computing device, or combination thereof exceeding or falling below a defined threshold.

7. The method of claim 1, further including executing the machine learning logic to learn, in association with the health data and the user activity data, scheduling data, contextual data, and a current environment of the user.

\* \* \* \* \*